US006465469B1

(12) United States Patent
Barberich et al.

(10) Patent No.: US 6,465,469 B1
(45) Date of Patent: Oct. 15, 2002

(54) S-HYDROXYNEFAZODONE

(75) Inventors: Timothy J. Barberich, Concord; Paul D. Rubin, Sudbury; William E. Yelle, Littleton, all of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/545,475

(22) Filed: Apr. 7, 2000

Related U.S. Application Data

(60) Provisional application No. 60/128,481, filed on Apr. 9, 1999.

(51) Int. Cl.$^7$ .................. A61K 31/525; A61P 25/24
(52) U.S. Cl. .................. 514/254.05; 544/366
(58) Field of Search .................. 544/366; 514/254.05

(56) References Cited

U.S. PATENT DOCUMENTS

| | | | |
|---|---|---|---|
| 4,338,317 A | 7/1982 | Temple et al. | 424/250 |
| 4,613,600 A | 9/1986 | Gammans et al. | 514/252 |
| 5,116,852 A | 5/1992 | Gammans | 514/359 |
| 5,256,664 A | 10/1993 | Mayol et al. | 514/252 |
| 5,691,324 A | 11/1997 | Sandyk | 514/159 |
| 5,767,275 A | 6/1998 | Nigro et al. | 544/366 |
| 5,788,986 A | * 8/1998 | Dodman et al. | 424/451 |
| 5,852,020 A | 12/1998 | Marcus et al. | 514/252 |
| 5,854,248 A | 12/1998 | Marcus et al. | 514/255 |

FOREIGN PATENT DOCUMENTS

EP          0769297 A1       4/1997

OTHER PUBLICATIONS

"Clinical Pharmacokinetics of Nefazodene," Green et al, Clinical. Pharmacokinetics, Oct. 30, 1997, pp. 260–275.
"Single and Multiple Dose Pharmacokinetics of Nefazodone in Subjects Classified as Extensive and Poor Metabolizers of Dextromethorphan," Barbahaiya et al., British Journal of Clinical Pharmacology, 1996, 42:573–581.
"Attenuation of the Prolactin–Stimulating and Hyperthermic Effects of Nefazodone After Subacute Treatment," Walsh et al., Journal of Clinical Psychopharmacology, 1994, vol. 14, No. 4, pp. 268–273.
"In Vitro Binding Profile of Modern Antidepressants and their Metabolites: Correlation Between Affinities at Various Receptors," Knight et al., Society of Neuroscience, vol. 22, 1996 pp. 179.
"Nefazodone: Structure, Mode of Action and Pharmacokinetics," Malik, Journal of Psychopharmacology, 10 Supplement 1, (1996) pp. 1–4.
"A Study of the Effect of Age and Gender on the Pharmacokinetics of Nefazodone After Single and Multiple Doses," Barbhaiya et al., Journal of Clinical Psychopharmacology, 1996, vol. 16, No. 1, pp. 19–25.
"Characterization of the Metabolites of the Antidepressant Drug Nefazodone in Human Urine and Plasma," Mayol et al., Drug Metabolism and Disposition, 1994, vol. 22, No. 2, pp. 304–311.
"High–Performance Liquid Chromatographic Method for the Determination of Nefazodone and Its Metabolites in Human Plasma Using Laboratory Robotics," Franc, et al., Journal of Chromatography, 570 (1991) pp. 129–138.
Cyr et al., "Nefazodone: Its Place Among Antidepressants", Annals of Pharmaco Therapy, Sep. 1, 1996, pp. 1006–1012.
Nacca et al., "Brain–to–blood partition and in vivo inhibition of 5–hydroxytryptamine reuptake and quipazine–mediated behaviour of nefazodone and its main active metabolites in rodents", British Journal of Pharmacology (1988) 125, pp. 1617–1623.

* cited by examiner

*Primary Examiner*—Mukund J. Shah
*Assistant Examiner*—Hong Liu
(74) *Attorney, Agent, or Firm*—Mary Louise Gioeni, Esq.; Heslin Rothenberg Farley & Mesiti P.C.

(57) ABSTRACT

The S-isomer of the hydroxy metabolite of nefazodone, S-hydroxynefazodone, is an effective treatment for depression which does not give rise to the adverse effects associated with nefazodone. S-hydroxynefazodone is also useful in the treatment of migraine headaches, panic disorders, post traumatic stress disorder and sleep disorders.

20 Claims, No Drawings

S-HYDROXYNEFAZODONE

CROSS-REFERENCE TO RELATED APPLICATIONS

This application claims the benefit of U.S. Provisional Application No. 60/128,481, filed Apr. 9, 1999.

FIELD OF THE INVENTION

The present invention relates to methods of treating depression using S-hydroxynefazodone and pharmaceutical compositions containing S-hydroxynefazodone.

BACKGROUND OF THE INVENTION

Nefazodone, or 2- [3-[4-(3-chlorophenyl)1-piperazinyl] propyl]-5-ethyl-2,4-dihydro-4-(phenoxyethyl)-3H-1,2,4-triazol-3-one is approved for the treatment of depression by the United States Food and Drug Administration. It is available under the trade name SERZONE® from Bristol-Myers Squibb. Nefazodone has the structure of Formula I:

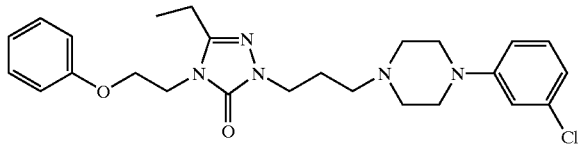

I

Studies have shown that nefazodone is extensively metabolized in the body. (See, for example, Green, D. S. and Barbhaiya, R. H., Drug Disposition, 1997, 260–275 (1997)). One of these metabolites is the hydroxylated derivative 2-[3-[4-(3-chlorophenyl)1-piperazinyl]propyl]-5-(1-hydroxyethyl)-2,4-dihydro-4-(phenoxyethyl)-3H-1,2,4-triazol-3-one, II, CAS Registry Number 98159-82-1, also known as hydroxynefazodone.

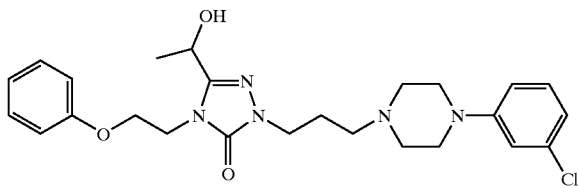

II

The stereochemistry of the metabolite II has not to date been defined in the literature. It is believed that the hydroxy metabolite of nefazodone contributes to the therapeutic activity of nefazodone (Malik, K., Journal of Psychopharmacology 1–4 (1996). Use of hydroxynefazodone as an antidepressant is disclosed in U.S. Pat. No. 4,613,600. Neither hydroxynefazodone (racemic) nor either of its stereoisomers is commercially available at the present time.

Preclinical studies have shown that nefazodone inhibits neuronal uptake of serotonin and norepinephrine. Nefazodone occupies central 5-HT$_2$ receptors at nanomolar concentrations, and acts as an antagonist at this receptor.

Nefazodone has been shown to antagonize alpha$_1$-adrenergic receptors, a property which may be associated with postural hypotension. In vitro binding studies showed that nefazodone had no significant affinity for the following receptors; alpha$_2$ and beta adrenergic, 5-HT$_{1A}$, cholinergic, dopaminergic, or benzodiazepine.

Nefazodone hydrochloride is rapidly and completely adsorbed but because of the extensive metabolism discussed above, its absolute bioavailability is low, about 20%, and variable. Peak plasma concentrations occur at about one hour and the half-life of nefazodone is 2–4 hours.

Both nefazodone and hydroxynefazodone exhibit nonlinear kinetics for both dose and time, with AUC and C$_{max}$ increasing more than proportionally with dose increases and more than expected upon multiple dosing over time, compared to single dosing.

The primary clinical use of nefazodone is in the treatment of depression. Use of nefazodone for treatment of various psychiatric illnesses has been disclosed in the patent literature. The term "psychiatric illness" is defined herein to include depression, sleep disorder involving decreased REM sleep and/or decreased slow wave sleep, panic disorder, recurrent headache disorder, post traumatic stress disorder, affective disorder, cerebral function disorders and obesity and weight gain. Nefazodone for the treatment of headache disorders is described in U.S. Pat. No. 5,854,248, for the treatment of post traumatic stress disorder, in U.S. Pat. No. 5,852,020, for the treatment of sleep disorders in U.S. Pat. No. 5,116,852, and for treating panic disorders, in European Patent application EP 769 297.

While nefazodone can be an effective treatment for depression, sleep disorders, post traumatic stress disorder and panic disorders, it can give rise to certain adverse effects. The most frequently reported adverse effects associated with nefazodone are headaches, dry mouth, somnolence, nausea and dizziness. Other adverse affects are headache, asthenia, infection, flu syndrome, chills, fever, neck rigidity, hypotension, pruritus, rash, nausea, constipation, dyspepsia, diarrhea, increased appetite, nausea and vomiting, peripheral edema, thirst, arthralgia, insomnia, lightheadedness, confusion, memory impairment, paresthesia, vasodilatation, abnormal dreams, decreased concentration, ataxia, incoordination, psychomotor retardation, tremor, hypertonia, decreased libido, pharyngitis, cough, blurred vision, abnormal vision, tinnitus, taste perversion, visual field defect, urinary frequency, urinary tract infection, urinary retention, vaginitis and breast pain. In addition, nefazodone is known to cause sinus bradycardia and postural hypotension.

It is therefore desirable to find a compound with the advantages of nefazodone which does not have the above described adverse effects.

Formation of hydroxynefazodone occurs in the liver through the enzymes of the P450 system, specifically CYP3A4, and nefazodone is an inhibitor of CYP3A4. Other drugs which inhibit the CYP3A4 isozyme may interfere with the formation of this metabolite. In addition, coadministration of another drug metabolized by CYP3A4 may lead to elevated blood concentrations of one or both drugs. For example, known inhibitors of CYP3A4, such as erythromycin, ketoconazole, and cimetidine, may interfere with hydroxylation of nefazodone. On the other hand, the disposition of drugs metabolized by CYP3A4, such as terfenadine and haloperidol, may be interfered with by nefazodone, and compounds which are inducers of CYP3A4 may cause faster metabolism of nefazodone when coadministered.

It would be desirable to find a compound with the advantages of nefazodone, but with fewer drug-drug interactions.

SUMMARY OF THE INVENTION

It has now been discovered that the S-isomer of the hydroxy metabolite of nefazodone, S-hydroxynefazodone, is an effective treatment for depression which does not give rise to the adverse effects associated with nefazodone. Therefore, in one aspect, the present invention relates to a method of treating depression, comprising administering to a person a need of such therapy a therapeutically effective amount of S-hydroxynefazodone or a pharmaceutically acceptable salt thereof.

It has also been discovered that the S-isomer of hydroxynefazodone is useful in the treatment of sleep disorders. In another aspect, the present invention relates to a method of treating sleep disorders involving decreased REM sleep and/or decreased slow wave sleep. The method comprises administering to a person in need of such therapy a therapeutically effective amount of S-hydroxynefazodone. Particular sleep disorders of interest are nocturnal myoclonus, REM sleep interruptions, jet-lag, shift workers' sleep disturbances, dysomnia, night terrors, insomnias of depression, and sleep walking disorders.

It has also been discovered that the S-isomer of hydroxynefazodone is useful in the treatment of panic disorders. In another aspect, the present invention relates to a method for alleviation of panic disorders comprising administering to a person in need of such therapy a therapeutically effective amount of S-hydroxynefazodone or pharmaceutically acceptable salt thereof Panic disorders of interest are panic attacks, agoraphobia, and phobic anxiety.

It has also been discovered that the S-isomer of hydroxynefazodone is useful in the treatment of recurrent headache disorders. In another aspect, the present invention relates to a method of treating recurrent headache disorders comprising administering to a person in need of such therapy a therapeutically effective dose of S-hydroxy nefazodone or a pharmaceutically acceptable salt thereof Recurrent headache disorders of interest are vascular headache, migraine headache, and chronic daily headache.

It has also been discovered that the S-isomer of hydroxynefazodone is useful in the treatment of post traumatic stress disorder. In another aspect, the present invention relates to a method of treating post traumatic stress disorder, comprising administering to a person in need of such therapy a therapeutically effective dose of S-hydroxynefazodone or a pharmaceutically acceptable salt thereof Symptoms of post traumatic stress disorder alleviated by treatment with S-hydroxynefazodone are depression, hostility, and sleep disturbance.

It has also been discovered that the S-isomer of hydroxynefazodone is useful in the treatment of affective disorders. These affective disorders include but are not limited to, attention deficit disorder and attention deficit disorder with hyperactivity. It has also been discovered that the S-isomer of hydroxynefazodone is useful in the treatment of obesity or weight gain.

It has also been discovered that the S-isomer of hydroxynefazodone is useful in the treatment of cerebral function disorders including, but not limited to, senile dementia, Parkinson's disease, epilepsy, Alzheimer's disease, amnesia/amnestic syndrome, autism and schizophrenia; disorders ameliorated by inhibition of neuronal monamine reuptake; and pain, particularly chronic pain. The invention further encompasses the treatment or prevention of obsessive-compulsive disorder, substance abuse, premenstrual syndrome, anxiety, eating disorders. The terms "obsessive-compulsive disorder", "substance abuse", "pre-menstrual syndrome", "anxiety", and "eating disorders" are used herein consistent with their accepted meanings in the art. See, e.g., DSM-IV (*Diagnostic and Statistical Manual*, fourth edition). The terms "methods of treating or preventing" when used in connection with these disorders means amelioration, prevention or relief from the symptoms and/or effects associated with these disorders. Without being limited by any theory, the treatment or prevention of certain of these disorders may be related to the activity of the active ingredient(s) as inhibitors of serotonin uptake.

In a preferred embodiment, S-hydroxynefazodone is administered orally, in an amount from about 25 mg to about 1000 mg per day, more preferably from about 200 mg per day to about 600 mg per day. A preferred dosage form is tablets or capsules.

In yet another aspect, the present invention relates to pharmaceutical compositions comprising S-hydroxynefazodone, or a pharmaceutically acceptable salt thereof. In a preferred embodiment, the composition also contains a pharmaceutically acceptable carrier.

In a further aspect, the invention relates to S-hydroxynefazodone, substantially free of R-hydroxynefazodone, or a pharmaceutically acceptable salt thereof

DETAILED DESCRIPTION OF THE INVENTION

The active compound of the methods and compositions of the present invention is S-hydroxynefazodone. Hydroxynefazodone contains a single chiral center, and therefore exists in an S- and an R-configuration. Neither of the enantiomers has been described in the literature. The structure of S-hydroxynefazodone is shown in Formula

III

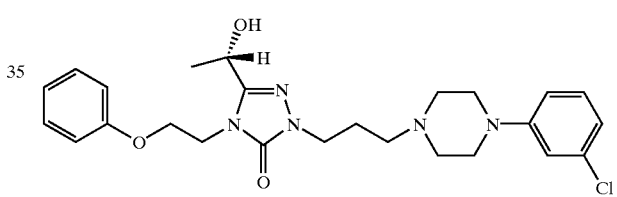

The S-hydroxynefazodone utilized for the methods and compositions of the present invention is substantially free of the R-stereoisomer of hydroxynefazodone, R-hydroxynefazodone. The term "substantially free of the R-stereoisomer" as used herein means that the compound and compositions of the present invention contain a significantly greater proportion of the S-isomer of hydroxynefazodone in relation to the R-isomer of hydroxynefazodone. In a preferred embodiment of the present invention, the compositions contain at least 90% by weight of S-hydroxynefazodone and 10% by weight or less of R-hydroxynefazodone. More preferably, the compositions contain at least 98% by weight of S-hydroxynefazodone and 2% by weight or less of R-hydroxy nefazodone, and in this case, the term "substantially free of the R-isomer" means that the compositions contain at least 98% by weight of S-hydroxynefazodone and 2% by weight or less of R-hydroxynefazodone. These percentages are based upon the total amount of hydroxynefazodone in the composition. The terms "substantially optically pure S-isomer of hydroxynefazodone" or "substantially optically pure S-hydroxy nefazodone" and "optically pure R-isomer of hydroxynefazodone" and "optically pure R-hydroxynefazodone" are also encompassed by the above-described amounts.

The present method encompasses a method of treating depression which comprises administering to a human in need of such therapy, an amount of S-hydroxy-nefazodone or pharmaceutically acceptable salt thereof, said amount being sufficient to alleviate the symptoms of depression. Depression is characterized by changes in mood, and by feeling of intense sadness or pessimistic worry. Symptoms include insomnia, anorexia, mental slowing and loss of drive, enthusiasm, and libido.

The present invention further encompasses a method of treating sleep disorders involving decreased REM sleep and/or decreased slow wave sleep, which comprises administering to a human in need of such therapy an amount of S-hydroxynefazodone or a pharmaceutically acceptable salt thereof, said amount being sufficient to alleviate the symptoms of sleep disorders. Sleep disorders of particular interest in humans include nocturnal myoclonus, REM sleep interruptions, jet-lag, shift workers' sleep disturbances, dysomnia, night terrors, insomnias of depression, and sleep walking disorders.

The present invention further encompasses a method of treating headache disorders which comprises administering to a human in need of such therapy an amount of S-hydroxynefazodone or a pharmaceutically acceptable salt thereof, said amount being sufficient to alleviate the symptoms of headache disorders. Headache disorders are defined as paroxysmal disorders characterized by recurrent attacks of headaches, with or without associated visual and gastrointestinal disturbances. Particular headache disorders of interest are vascular headache, migraine headache and chronic daily headache.

The present invention further encompasses a method of treating post traumatic stress disorder, which comprises administering to a human in need of such therapy a therapeutically effective dose of S-hydroxynefazodone or pharmaceutically acceptable salt thereof, such amount being sufficient to alleviate the symptoms of post traumatic stress disorder (PTSD). Symptoms of PTSD include depression, hostility and sleep disturbances. PTSD is defined by DSM-IV as an anxiety disorder which develops following exposure to an extremely traumatic event. The diagnosis of PTSD is made when the following core symptoms follow exposure to the trauma: the traumatic event is persistently re-experienced (via intrusive thoughts, dreams, flashbacks or internal and external cues); there is persistent avoidance of evidence associated with the trauma or generalized psychological numbing and isolation; and there is widespread psychologic arousal which was not present prior to the trauma.

The present invention further encompasses a method of treating panic disorders, including panic attacks, agoraphobia and phobic anxiety, which comprises administering to a human in need of such therapy a therapeutically effective dose of S-hydroxynefazodone or pharmaceutically acceptable salt thereof, such amount being sufficient to alleviate the symptoms of panic disorders. Panic disorders are defined as the frequent occurrence of panic attacks.

The present invention further encompasses a method of treating affective disorders comprising administering to a person a need of such therapy a therapeutically effective amount of S-hydroxynefazodone or a pharmaceutically acceptable salt thereof, such amount being sufficient to alleviate the symptoms of affective disorders. Affective disorders include attention deficit disorder, attention deficit disorder with hyperactivity, and bipolar and manic conditions. The terms "attention deficits disorder (ADD) and attention deficit disorder with hyperactivity" (ADDH), or attention deficit/hyperactivity disorder (AD/HM), are used herein in accordance with the accepted meanings as found in DSM-IV.

The present invention further encompasses a method of treating obesity or weight gain comprising administering to a person a need of such therapy a therapeutically effective amount of S-hydroxynefazodone or a pharmaceutically acceptable salt thereof, such amount being sufficient to provide reduction of weight, relief from being overweight, relief from gaining weight, or relief from obesity.

The present invention further encompasses a method of treating cerebral function disorders comprising administering to a person a need of such therapy a therapeutically effective amount of S-hydroxynefazodone or a pharmaceutically acceptable salt thereof, such amount being sufficient to provide relief from disease states associated with cerebral function disorders involving intellectual deficits including, but not limited to, senile dementia, Alzheimer's type dementia, memory loss, amnesia/amnestic syndrome, disturbances of consciousness, coma lowering of attention, speech disorders, Parkinson's disease, Lennox syndrome, autism, hyperkinetic syndrome and schizophrenia. Also within the meaning of cerebral function disorders are disorders caused by cerebrovascular diseases including, but not limited to, cerebral infarction, cerebral bleeding, cerebral arteriosclerosis, cerebral venous thrombosis, senile dementia, coma, lowering of attention, and speech disorders. Symptoms of disease states associated with abnormal neuronal monoamine levels are reduced by way of neuronal monoamine reuptake inhibition by S-hydroxy nefazodone. These monoamines include, but are not limited to, noradrenaline (or norepinephrine), serotonin and dopamine. Disorders treated by neuronal monoamine reuptake inhibition include, but are not limited to, Parkinson's disease and epilepsy. The symptoms of Parkinson's disease include, but are not limited to, slowly increasing disability in purposeful movement, tremors, bradykinesia, rigidity, and a disturbance of posture in humans.

The present invention also encompasses a pharmaceutical composition which comprises a pharmaceutically acceptable carrier and a therapeutically effective amount of S-hydroxynefazodone or a pharmaceutically salt thereof Preferably the composition is formulated for oral administration. More preferably the composition is in the form of a tablet or capsule.

Administration of S-hydroxynefazodone results in fewer adverse effects compared with administration of nefazodone. One or more of the following adverse effects of nefazodone may be avoided by the administration of S-hydroxynefazodone: headache, asthenia, infection, flu syndrome, chills, fever, neck rigidity, postural hypotension, hypotension, pruritus, rash, dry mouth, nausea, constipation, dyspepsia, diarrhea, increased appetite, nausea and vomiting, peripheral edema, thirst, arthralgia, somnolence, dizziness, insomnia, lightheadedness, confusion, memory impairment, paresthesia, vasodilatation, abnormal dreams, concentration decreased, ataxia, incoordination, psychomotor retardation, tremor, hypertonia, libido decreased, pharyngitis, cough increased, blurred vision, abnormal vision, tinnitus, taste perversion, visual field defect, urinary frequency, urinary tract infection, urinary retention, vaginitis and breast pain.

The magnitude of a prophylactic or therapeutic dose of S-hydroxynefazodone will vary with the nature and severity of the condition to be treated and the route of administration. The dose, and perhaps the dose frequency, will also vary according to the age, body weight and response of the individual patient. In general, the total daily dose ranges from about 25 mg per day to about 1000 mg per day, preferably about 100 mg per day to about 600 mg per day, in single or divided doses. It is further recommended that children, patients over 65 years old, and those with impaired renal or hepatic function, initially receive low doses and that the dosage by titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Any suitable route of administration may be employed for providing the patient with an effective dosage of S-hydroxynefazodone. For example, oral, rectal, parenteral (including subcutaneous, intramuscular, and intravenous) routes may be employed. Dosage forms include tablets, troches, dispersions, suspensions, solutions, capsules and patches.

The pharmaceutical compositions of the present invention comprise S-hydroxy nefazodone or a pharmaceutically acceptable salt thereof as an active ingredient, and may also contain a pharmaceutically acceptable carrier and, optionally, other therapeutic ingredients. The term pharmaceutically acceptable salts refers to salts prepared from pharmaceutically acceptable non-toxic acids including inorganic acids and organic acids. Exemplary acids that form pharmaceutically acceptable salts with S-hydroxynefazodone for use in the compositions of the present invention are acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid andp-toluenesulfonic acid. The hydrochloric acid salt is particularly preferred.

Compositions suitable for oral, rectal, and parenteral administration are encompassed by the present invention. A preferred route of administration is oral. The compositions may be conveniently presented in unit dosage form and prepared by any of the methods well known in the art of pharmacy. Preferred unit dosage formulations are those containing an effective dose, or an appropriate fraction thereof, of the active ingredient, S-hydroxynefazodone, or a pharmaceutically acceptable salt thereof.

The compositions of the present invention may also include a pharmaceutically acceptable carrier. The carrier may take a wide variety of forms, depending on the forms preparation desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous techniques. Oral and parenteral sustained release dosage forms may also be used.

Oral syrups, as well as other oral liquid formulations, are well known to those skilled in the art, and general methods for preparing them are found in any standard pharmacy school textbook, for example Remington: *The Science and Practice of Pharmacy*. Chapter 86 of the 19th edition of Remington entitled "Solutions, Emulsions, Suspensions and Extracts" describes in complete detail the preparation of syrups (pages 1503–1505) and other oral liquids. Similarly, sustained release formulation is well known in the art, and Chapter 94 of the same reference, entitled "Sustained-Release Drug Delivery Systems," describes the more common types of oral and parenteral sustained-release dosage forms (pages 1660–1675.) The relevant disclosure, Chapters 84 and 96, is incorporated herein by reference. Because they reduce peak plasma concentrations, as compared to conventional oral dosage forms, controlled release dosage forms are particularly useful for providing a therapeutic plasma concentration of S-hydroxynefazadone while avoiding the side effects associated with high peak plasma concentrations that occur with conventional dosage forms.

The present invention further encompasses S-hydroxynefazodone, substantially free of R-hydroxynefazodone. Preparation of S-hydroxynefazodone is illustrated in Example 1. If necessary, the S- and R-isomers of hydroxynefazodone may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomer may be synthesized by asymmetric synthesis using optically active reagents, substrates, catalysts or solvents, or by converting on enantiomer to the other by asymmetric transformation.

EXAMPLES

Example 1
Preparation of S-hydroxynefazodone

The general method is as follows: The hydrazine derivative of a protected S-(+) lactic acid ester is first reacted with a substituted isocyanate to give a semicarbazone intermediate. The semicarbazone is then cyclized to a triazolone and the triazolone is alkylated with a chloroalkylpiperazine. Finally, the protecting group is cleaved with dilute acid to yield S-hydroxynefazodone.

The methoxymethyl ether derivative of S-(+) methyl lactate is prepared by refluxing one equivalent of S-(+) methyl lactate, 5 equivalents of methal (dimethoxymethane) and a catalytic amount (0.1 g) of p-toluenesulfonic in methylene chloride for several days and removing the methanol produced by azeotropic distillation. Following completion of the reaction, a small amount of triethylamine is added and the reaction mixture is washed with brine, the organic phase dried ($K_2CO_3$) and concentrated in vacuo to a residue which is distilled to yield the crude methoxymethyl ether derivative of S-(+) methyl lactate. This crude material is used without further purification.

The methoxymethyl ether derivative of S-(+) methyl lactate (6.3 g) is added dropwise to a stirred, cold (0° C.) solution of hydrazine (1.36 g, 1.35 mL) in 10 mL methanol. After completion of the addition, the reaction mixture is placed in a freezer (approximately-10° C.) for 18 hours. The methanol is then removed under reduced pressure and the residue distilled at 0.8 Torr to give the hydrazide product, b. p. 90° C.–115° C.

A solution of trimethylsilyl azide (2.05 g, 2.36 mL, 1.1 equivalent) in 1 mL toluene is added dropwise to a hot (approximately 100° C.) solution of 3-phenoxy propionyl chloride in 2 mL toluene. This reaction mixture is heated at 95° C.–100° C. for 3.5 hours after addition of the azide reagent. The toluene and by-product trimethylsilyl chloride are removed by distillation. The residual isocyanate intermediate is added to a cold (0° C.) solution of (2.4 g, 16.2 mmole, 1.0 equivalent) in approximately 5 mL methylene chloride. This reaction mixture is stored in a freezer for 16 hours during which time the semicarbazide product crystallizes from solution. Recrystallization from 1,2-dichloroethane gives the semicarbazide.

The semicarbazide is cyclized to a triazolone ether intermediate by refluxing in 5% KOH solution. The semicarbazide 5 (3.1 g) is dissolved in approximately 35 mL 5% KOH solution. The reaction mixture is refluxed under nitrogen for 5 hours. At this point the reaction mixture is cooled and the pH adjusted to approximately 8 using glacial accetic acid. This aqueous solution is then extracted with methylene chloride and the combined organic extracts dried and concentrated in vacuo. Recrystallization from ethanol-water yields the triazolone ether.

The triazolone ether intermediate (2.5 g), 1-(3-chloropropyl)4-(3-chlorophenyl)piperazine (2.45 g), potassium carbonate (4.7 g), tetrabutylammonium hydrogen sulfate (0.18 g) and potassium iodide (0.02 g) are refluxed in 20 mL acetonitrile for 18 hours. The reaction mixture is then filtered and the filtrate concentrated in vacuo to a residue which is heated in 10 mL of 6N HCL at 60° C. for 15 minutes. This acidic mixture is then chilled to 0° C. and made basic by the dropwise addition of 50% sodium hydroxide solution. This basic mixture is extracted with methylene chloride, dried and concentrated in vacuo. Flash chromatography (4% methanollmethylene chloride) affords S-hydroxynefazodone.

The basic form of S-hydroxynefazodone can be converted to the hydrochloride salt by treatment of an ethanol solution of S-hydroxynefazodone with ethanolic HCl.

Example 2

250 mg Tablets

Composition per tablet:

| S-hydroxynefazodone | 250 mg |
| croscarmellose | 60 mg |
| colloidal silicon dioxide | 8 mg |
| magnesium stearate | 1 mg |
| microcrystalline cellulose | 190 mg |
| croscarmellose | 15 mg |
| talc | 10 mg |
| Total | 534 mg |

S-hydroxynefazodone and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

Example 3

200 mg Tablets

Composition per unit dosage:

| S-hydroxynefazodone | 200 mg |
| pregelatinized starch | 200 mg |
| microcrystalline cellulose | 25 mg |
| povidone | 15 mg |
| croscarmellose | 10 mg |
| magnesium stearate | 3.75 mg |
| FD&C yellow #2 lake | 2.5 mg |
| Water | (5 mL) |
| Total | 456.25 mg |

The ingredients above are mixed well in the proportions shown in a high shear mixer until uniform granules result. The mixture is tray-dried at 40° C. under vacuum until the desired consistency is reached. The granules are milled to less than 60 mesh using a screen miill and compressed into tablets.

S-hydroxynefazodone exhibits selective central nervous system effects associated with antidepressant activity according to conventional in vivo test systems such as those listed below:

Suppression of Conditioned Avoidance Response (CAR) [Albert, et al., Pharmacologist, 4, 152 (1962)].

Prevention of Reserpinc Ptosis in Mice (anti-depressant test) [Niemegeers, Industrial Pharmacology, Vol 2—Antidepressants, edit. By S. Fielding and H. Lat. Pp. 73–98, Futura, New York, N.Y. (1975).]

In these tests, S-hydroxynefazodone suppresses CAR in the rat and prevents, but does not reverse, reserpine ptosis in the mouse. Such activity is characteristic of most clinically useful antidepressant agents.

As fuirther indication of the psychotropic activity and specificity of S-hydroxy nefazodone, state of the art in vitro central nervous system receptor binding methodology can be employed. Certain compounds (commonly referred to as ligands) have been identified which preferentially bind to specific high affinity sites in brain tissue dealing with psychotropic activity or in brain tissue dealing with psychotropic activity or potential for side effects. Inhibition of radiolabeled ligand binding to such specific high affinity sites is considered a measure of a compound's ability to affect corresponding central nervous system function or cause side effects in vivo.

The following tests, as well as others, can be employed in developing a profile of the psychotropic activity of S-hydroxynefazodone.

Dopamine [Burt, et al., Molecular Pharmacology, 12,800 (1976); Science, 196, 326 (1977); Creese, et al., Science 192, 481 (1976)].

Cholinergic [Yaoamura, et al., Proceedings National Academy of Science, USA 71.1725 (1974.)]

Alpha-receptor [Crews, et al., Science, 202:322 (1978); Rosenblatt, et al., Brian Research, 160: 186 (1979); U'Pritchard, et al., Science, 199:197 (1978); U'Pritchard, et al. Molecular Pharmacology, 13:454 (1977).]

Serotonin Type 2 [Peroutka and Snyder, Molecular Pharmacology, 18:687 (1979).

According to the foregoing assays, S-hydroxynefazodone inhibits serotonin binding and is relatively inactive with respect to dopamine receptor binding, cholinergic receptor binding, and alpha-receptor binding. The latter is particularly significant in that drugs with high affinity for alpha-receptors relative to serotonin type 2 receptors are likely to cause side effects such as sedation and blood pressure lowering. Thus, because S-hydroxynefazodone gives similar binding and biological test results, it is considered a useful antidepressant.

What is claimed is:

1. A method for treating one or more psychiatric illnesses chosen from the group consisting of depression, sleep disorder involving decreased REM sleep and/or decreased slow wave sleep, panic disorder, recurrent headache disorder, and post traumatic stress disorder, said method comprising administering to a person afflicted with said one or more psychiatric illnesses a therapeutically effective amount of S-hydroxynefazodone or a pharmaceutically acceptable salt thereof.

2. A method according to claim 1 wherein said psychiatric illness is depression.

3. A method according to claim 1 wherein said psychiatric illness is sleep disorder involving decreased REM sleep and/or decreased slow wave sleep.

4. A method according to claim 3 wherein the sleep disorder is selected from the group consisting of nocturnal myoclonus, REM sleep interruptions, jet lag, shift workers' sleep disturbances, dysomnia, night terrors, insomnias of depression, and sleep walking disorders.

5. A method according to claim 1 wherein said psychiatric illness is panic disorder.

6. A method according to claim 5 wherein the panic disorder is characterized by panic attacks.

7. A method according to claim 5 wherein the panic disorder is characterized by agoraphobia.

8. A method according to claim 5 wherein the panic disorder is characterized by phobic anxiety.

9. A method according to claim 1 wherein said psychiatric illness is recurrent headache disorder.

10. A method according to claim 9 wherein the headache disorder is vascular headache.

11. A method according to claim 9 wherein the recurrent headache disorder is migraine headache.

12. A method according to claim 9 wherein the recurrent headache disorder is chronic daily headache.

13. A method according to claim 1 wherein said psychiatric illness is post traumatic stress disorder.

14. A method according to claim 13 wherein a major symptom of the post traumatic stress disorder is depression.

15. A method according to claim 13 wherein a major symptom of the post traumatic stress disorder is hostility.

16. A method according to claim 13 wherein a major symptom of the post traumatic stress disorder is sleep disturbance.

17. A method according to claim 1 wherein S-hydroxynefazodone is administered orally.

18. A method according to claim 17 wherein the amount of S-hydroxynefazodone administered is from about 25 mg to about 1000 mg per day.

19. A method according to claim 17 wherein the amount of S-hydroxynefazodone administered is from about 200 mg per day to about 600 mg per day.

20. A method according to claim 1 wherein S-hydroxynefazodone hydrochloride is administered.

* * * * *